(12) United States Patent
Kohno

(10) Patent No.: US 8,758,251 B2
(45) Date of Patent: Jun. 24, 2014

(54) ULTRASOUND ENDOSCOPE

(75) Inventor: Shinichi Kohno, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 569 days.

(21) Appl. No.: 11/673,739

(22) Filed: Feb. 12, 2007

(65) Prior Publication Data

US 2007/0232922 A1    Oct. 4, 2007

(30) Foreign Application Priority Data

Feb. 16, 2006 (JP) ................................. 2006-039056
Mar. 22, 2006 (JP) ................................. 2006-078061

(51) Int. Cl.
*A61B 8/14* (2006.01)
*A61B 8/00* (2006.01)
*A61B 1/04* (2006.01)

(52) U.S. Cl.
USPC ............ 600/459; 600/109; 600/447; 600/462

(58) Field of Classification Search
USPC ......... 600/109, 122, 123, 437, 459, 462, 463, 600/447
See application file for complete search history.

(56) References Cited

U.S. PATENT DOCUMENTS

| | | | | |
|---|---|---|---|---|
| 5,471,988 | A * | 12/1995 | Fujio et al. | 600/439 |
| 6,149,598 | A * | 11/2000 | Tanaka | 600/462 |
| 6,338,717 | B1 * | 1/2002 | Ouchi | 600/462 |
| 2004/0082883 | A1 * | 4/2004 | Kohno | 601/2 |
| 2005/0222493 | A1 * | 10/2005 | Kohno | 600/107 |

FOREIGN PATENT DOCUMENTS

| | | |
|---|---|---|
| JP | 6-105847 A | 4/1994 |
| JP | 9-108224 A | 4/1997 |
| JP | 11-76155 A | 3/1999 |

(Continued)

OTHER PUBLICATIONS

Office Action issued Apr. 26, 2011, in Japanese Patent Application No. 2006-078061 (with partial English-language translation).

(Continued)

*Primary Examiner* — Long V. Le
*Assistant Examiner* — Katherine Fernandez
(74) *Attorney, Agent, or Firm* — Birch, Stewart, Kolasch & Birch, LLP

(57) ABSTRACT

An ultrasound endoscope having an ultrasound transducer mounted on a rigid tip end section at the distal end of an elongated endoscopic insert section, on the front side of a inclined casing wall section in which illumination windows and an optical image pickup assembly are fitted. For protrusion of a medical instrument into a body cavity, an instrument outlet of a biopsy channel is opened in a casing of the rigid tip end section in an obliquely upward direction from behind the ultrasound transducer. As far as a proximal end of the rigid tip end section, the biopsy channel is constituted by a flexible tube which is extended in the axial direction of the insert section and joined by way of a curved connecting pipe with a terminal passage which is formed internally of a casing of the rigid tip end section and inclined relative to the longitudinal axis of the latter. The instrument outlet is opened in a flat top surface of a plateau which is provided on the casing of the rigid tip end section on the rear side of the ultrasound transducer, the flat top surface of said plateau being located at a level lower than a top end the ultrasound transducer and the illumination windows fitted in the inclined casing wall section.

10 Claims, 13 Drawing Sheets

(56) References Cited

FOREIGN PATENT DOCUMENTS

| JP | 11-276422 | 10/1999 |
| JP | 2001-224550 A | 8/2001 |
| JP | 2002-238906 A | 8/2002 |
| JP | 2005-21197 | 1/2005 |

OTHER PUBLICATIONS

Office Action issued Apr. 26, 2011, in Japanese Patent Application No. 2006-039056 (with partial English-language translation).

* cited by examiner

FIG. 6
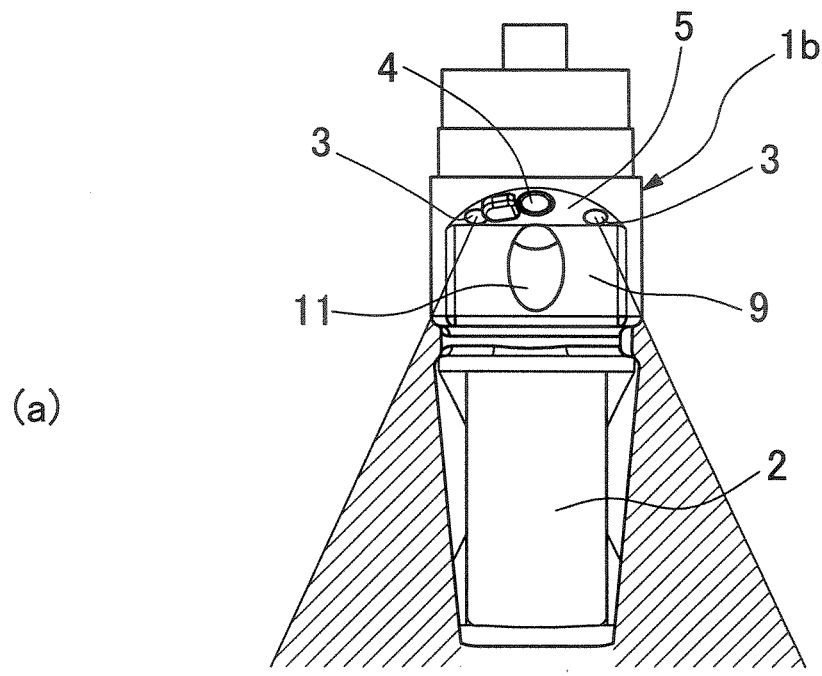
(a)
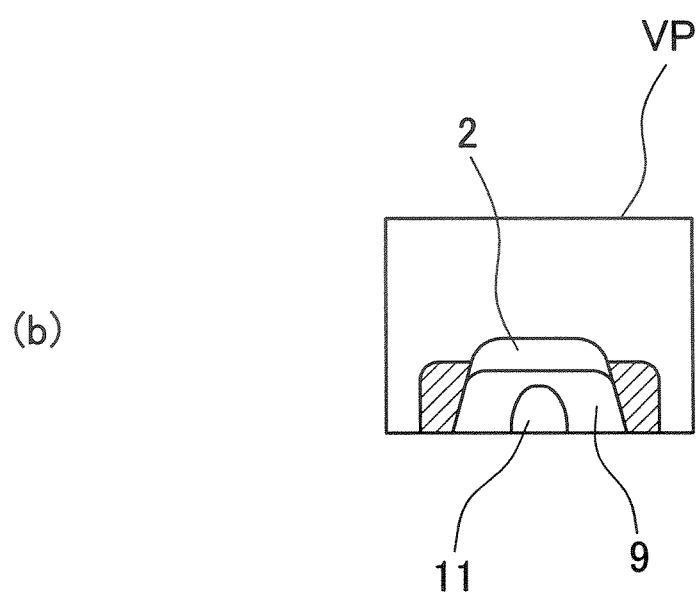
(b)

FIG. 10
(a) 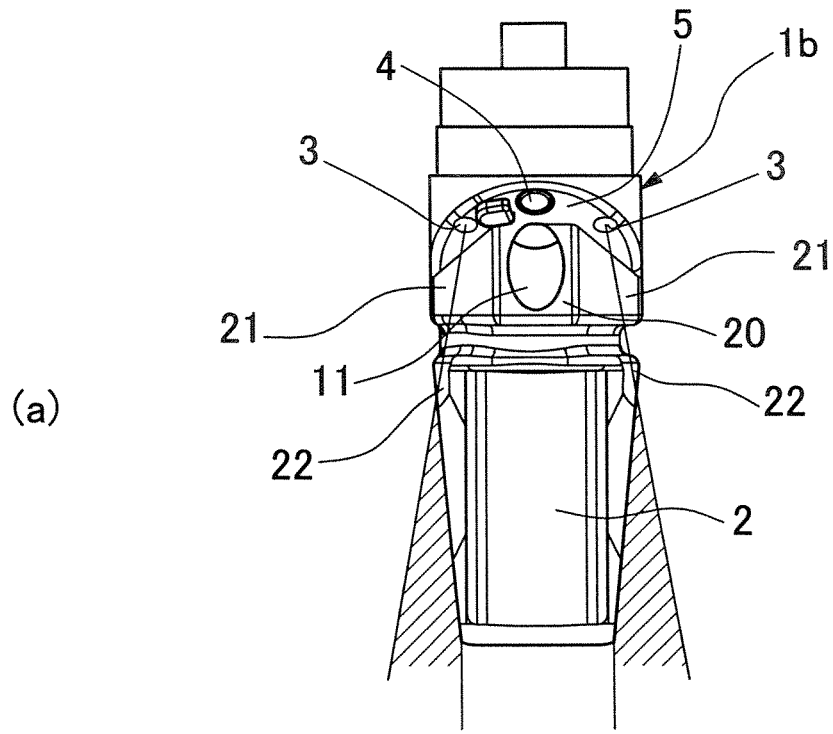
(b) 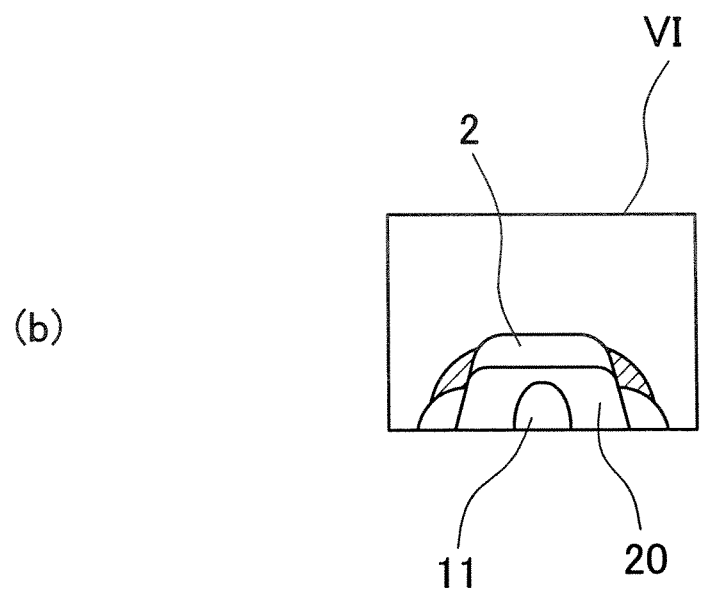

ULTRASOUND ENDOSCOPE

BACKGROUND OF THE INVENTION

1. Field of the Art

This invention relates to an ultrasound endoscope having an electronic scan type ultrasound transducer incorporated into a rigid tip end section at the distal end of an elongated insert section along with an optical observation means.

2. Prior Art

Ultrasound endoscopes have both an optical observation means and an ultrasound examination means on a rigid tip end section of an elongated flexible insert section to be inserted into a body cavity. The optical observation means is composed of illumination components and an optical image pickup system for observation of intracavitary sites of interest. Normally, picture images of an intracavitary site are captured by a solid-state image sensor. On the other hand, the ultrasound examination means is constituted by an ultrasound transducer which is categorized either as a mechanical scan type or as an electronic scan type depending upon the operating mode of the ultrasound transducer. An electronic scan type ultrasound transducer is provided with a plural number of transducer elements which are arrayed in a predetermined direction and are sequentially activated to make an ultrasound scan over a predetermined range.

As described in Japanese Laid-Open Patent Application H10-118072, for example, in the case of an ultrasound endoscope with an electronic scan type ultrasound transducer, an ultrasound transducer is mounted on a rigid tip end section at the distal end of an endoscopic insert section, and illumination or lighting components and an image pickup system of the optical observation means are mounted behind the ultrasound transducer. In that prior art ultrasound endoscope, a large number of ultrasound transducer elements are arrayed in a convexly arcuate shape in the axial direction of the rigid tip end section. The casing of the rigid tip end section is sloped upward behind the ultrasound transducer to provide a inclined casing wall section for fitting the illumination components and image pickup system of the optical observation means which has a view field in an obliquely upward direction, providing a slant view endoscope.

Tomographic information of body tissues can be obtained by activating the ultrasound transducer for an ultrasound scan. In case a disorder is found in body tissues, a treatment or sampling of body tissues can be made by the use of a puncture instrument. For this purpose, a biopsy channel is provided through the insert section of the endoscope for insertion of a biopsy or surgical or other medical instrument. The biopsy channel is constituted by a flexible tube up to a point immediately on the proximal side of the rigid tip end section of the insert section, namely, as far as a fore end of a bending section which is provided on the proximal side of the rigid tip end section to turn the latter into a desired direction. By the use of a connecting pipe, the flexible tube of the biopsy channel is connected to a tunnel-like terminal passage which is provided internally of the casing of the rigid tip end section. A fore end portion of the connecting pipe is inserted into the tunnel-like terminal passage while its rear end portion is projected into the bending section by a predetermined length, and fore end the flexible tube is joined with the rear end of the connecting pipe in the bending section by fitting engagement with the latter. Accordingly, the biopsy channel is constituted by a straight passage which is extended in the axial direction of the insert section as far as the angle section on the proximal side of the rigid tip end section. Past the bending section, the biopsy channel is constituted by a terminal passage which is turned upward or radially outward in the forward direction. An opening at the fore end of the tunnel-like passage forms an instrument outlet in the afore-mentioned inclined wall section of the casing of the rigid tip end section, in which illumination components and image pickup system of the optical observation means are fitted. Thus, a biopsy or surgical instrument which is projected out of the biopsy channel can be captured in the view field of the endoscopic observation means.

In case a diseased portion or a site of particular interest is spotted in body tissues under an ultrasound examination, for example, tissue cells are sampled for the purpose of close examination. A puncture instrument to be stabbed into an intracavitary wall for this purpose is normally provided with a sharp-pointed metal pipe needle of a predetermined length at one end of a flexible tube.

In order to control movement of the sharp-pointed puncture instrument in a safe and secure manner, it is monitored by the optical observation means until it comes into contact with an intracavitary wall. After penetration into an intracavitary wall, the puncture needle is monitored by the ultrasound examination means. The monitoring by the optical observation means is started as soon as the puncture instrument is led out of the instrument outlet opening of the biopsy channel. Once the puncture instrument is projected out of the instrument outlet, the inserted medical instrument should be monitored by the optical observation means every moment without a blind period in which the inserted medical instrument gets out of a view field of the monitoring optical observation means during a movement over a certain distance. Such a blind distance, if any, should be limited to a minimum. Further, the view field of the optical observation means can be limited depending upon the position of the instrument outlet which is opened in a casing wall of the rigid tip end section. Heretofore, from the standpoint of securing a suitable optical observation view field, the instrument outlet opening is opened in a inclined casing wall section in which the optical observation means is accommodated. That is to say, it has been the conventional practice to provide the instrument outlet of the biopsy channel in the proximity of the optical observation means.

Further, a terminal passage which leads to the instrument outlet plays an important role in stabilizing an inserted medical instrument and aiming same at a target point. For these functions, it is desirable for the terminal passage to have a sufficient length. If an inserted medical instrument gets out of the view field of the optical observation means over a certain distance after extrusion from the instrument outlet in the casing of the rigid tip end section, the unguided blind distance might give rise to not only safety problems but also problems in stabilizing and controlling movements of the inserted medical instrument at instant of protrusion through the instrument outlet of the biopsy channel.

As explained hereinbefore, normally an ultrasound transducer is mounted on a rigid tip end section of an ultrasound endoscope, on the front side of an optical observation means which is fitted in a inclined casing wall section and arranged to have a view field in an obliquely upward direction. However, in the case of an electronic scan type ultrasound transducer, a large number of ultrasound transducer elements are arrayed in a convexly arcuate shape in the axial direction of the rigid tip end section, so that the view field of the optical observation means is necessarily limited by the ultrasound transducer to a certain degree. In this regard, even if a casing wall with the instrument outlet opening is located within a view field of an optical observation means, it gives no affects in particular on the endoscopic observation by the optical observation means as long as it is in a range where the view field of the endoscopic observation means is limited by the ultrasound transducer.

SUMMARY OF THE INVENTION

With the foregoing situations in view, it is an object of the present invention to provide an ultrasound endoscope which is provided with a maximally elongated guide surface for an inserted medical instrument without restricting an optical observation view field and an ultrasound observation view field as well.

It is another object of the present invention to secure stability of an inserted medical instrument on protrusion from an instrument outlet opening at the distal end of a biopsy channel, with a minimal restriction of a view field by an optical observation system of the endoscope.

It is still another object of the present invention to improve controllability of an inserted medical instrument in aiming same at a target on protrusion from an instrument outlet opening at the distal end of a biopsy channel.

It is a further object of the present invention to provide an ultrasound endoscope which is capable of monitoring an inserted medical instrument up to a predetermined position after protrusion into a body cavity by way of clear intracavitary images captured through an optical observation system.

In order to achieve the above-stated objectives, according to the present invention, there is provided an ultrasound endoscope comprised of an electronic scan type ultrasound transducer having an array of ultrasound elements mounted on a rigid tip end section of an endoscopic insert section in an axial direction thereof, an instrument outlet of a biopsy channel opened in a casing of the rigid tip end section in an obliquely upward direction from behind the ultrasound transducer for protruding a medical instrument into a body cavity, and a inclined casing wall section provided further on the rear side of the instrument outlet for fitting optical observation means including illumination windows and an optical image pickup assembly, characterized in that: the instrument outlet of the biopsy channel is constituted by a flexible tube extending in axial direction of the insert section up to a proximal end portion of the rigid tip end section and having a fore distal end joined with a curved connecting pipe for connection to a terminal passage inclined relative to longitudinal axis of the rigid tip end section and sloped toward the instrument outlet; and a plateau is provided on the rigid tip end section between the ultrasound transducer and the inclined casing wall section, the plateau having a flat top surface at a level lower than the ultrasound transducer and the illumination windows of the optical observation means, and the instrument outlet of the biopsy channel is opened in the flat top surface of the plateau.

The ultrasound endoscope according to the present invention has an ultrasound transducer mounted on a front portion of a rigid tip end section of an elongated endoscopic insert section, with illumination windows and optical image pickup assembly fitted in a inclined casing wall section which is provided on the rear side of the ultrasound transducer. Here, the terms ☐front end☐ and ☐rear end☐ of the rigid tip end section mean front and rear ends in the axial direction, respectively, and it is the rear end of the rigid tip end section which is connected to an bending section of the endoscopic insert section. Further, right and left lateral sides are in a transverse direction which is perpendicular to the axial direction. A plateau with a flat top surface is provided between the ultrasound transducer and a inclined casing wall section in which an optical image pickup assembly is fitted, and an instrument outlet of a biopsy channel is opened in the flat top surface of the plateau. The flat top surface of the plateau is either disposed substantially parallel with the longitudinal axis of the rigid tip end section or sloped upward in the forward direction. The flat top surface of the plateau is formed contiguously on the front side of the inclined casing wall section in which the optical observation means is fitted, so that, in an application of a sloped form, it should not be inclined in the same direction as the inclined casing wall section. A transitional portion from the flat top surface to the inclined casing wall section is at a level which is at least lower than the illumination windows in the inclined casing wall section and a top end of the ultrasound transducer. The optical image pickup assembly which is fitted in the inclined casing wall section has a view field in an obliquely upward direction. In this instance, since the ultrasound transducer is mounted further on the front side of the flat top surface of the plateau, the view field of the optical observation means is restricted by the ultrasound transducer. Especially, in a case where transducer elements of an ultrasound transducer are arrayed in a convexly arcuate form, a middle portion of the transducer element array is raised to a height which partly restricts the optical observation view field. That is to say, there is no possibility of the optical observation view field being further restricted by the flat top surface of the plateau as long as the flat top surface is located within a range restricted by the ultrasound transducer.

The terminal passage of the biopsy channel is formed internally of a casing of the rigid tip end section in the form of a sloped passage turning upward or radially outward in the forward direction to guide an inserted medical instrument along the sloped passage. The longer the length of the guide passage, the higher becomes the stability of a medical instrument which is manipulated by an operator for protrusion into a body cavity. In the terminal passage leading to the instrument outlet of the biopsy channel, actually an inserted medical instrument is guided by a sloped passage portion which rises upward or radially outward in the forward direction, and not guided by other portions of the passage. Therefore, the terminal passage of the biopsy channel can be elongated by opening the instrument outlet in the flat top surface of the plateau which is disposed parallel with the longitudinal axis of the rigid tip end section, as compared with a case where the instrument outlet is opened in the inclined casing wall section in which an optical observation system is fitted.

In this connection, it has been the general practice to fit a couple of illumination windows in the inclined casing wall section, on the right and left sides of the optical observation system for the purpose of suppressing irregularities in illumination light level. That is to say, at least two illumination windows are fitted in the inclined casing wall section. However, the number of illumination windows is not limited to two, and one or more illumination windows may be provided in arbitrary positions other than the right and left sides of the optical observation system. Any way, illumination windows are located at a higher level than and at a short distance from the flat top surface in which the instrument outlet of the biopsy channel is opened. Therefore, the flat top surface can interfere with illumination light, increasing shadowed areas by blocking part of illumination light.

As mentioned hereinbefore, a plateau with a flat top surface with an instrument outlet opening is provided between an ultrasound examination means and an optical observation means which are mounted on a rigid tip end section at the distal end of an endoscopic insert section. If suffices for the flat top surface of the plateau to have a minimum breadth for installation of the instrument outlet, and walls at the right and left sides of the plateau are not necessarily required to be straight flat walls. Besides, except the instrument outlet, no other components are accommodated under the flat top surface.

For these reasons, the flat top surface of the plateau should preferably be limited to a minimum area which is necessary for installation of the instrument outlet. Right and left lateral sides of the plateau, on the opposite sides of the instrument outlet, are obliquely cut away to provide receded light guide walls, eliminating or minimizing those areas which would otherwise fall in the shadow of the top flat surface. In this connection, it is desirable to cut off the opposite right and left sides of the plateau obliquely in the lateral direction in forming receded light guide walls which open up an unobstructed path for light which is cast forward from the respective illumination windows. Nevertheless, the opposite sides of the plateau may be cut off at right angles or obliquely in the forward direction if desired. If necessary, additional illumination windows may be fitted in the receded light guide walls. Otherwise, an outlet of a fluid supply passage may be opened in the light guide walls.

The above and other objects, features and advantages of the present invention will become apparent from the following particular description of the invention, taken in conjunction with the accompanying drawings which show by way of example some preferred embodiments of the invention. Needless to say, the present invention should not be construed as being limited to particular forms which are shown in the drawings.

BRIEF DESCRIPTION OF THE DRAWINGS

In the accompanying drawings:

FIG. 6 is a schematic illustration explanatory of shadows which are cast by blockage of illumination light in case no receded light guide walls are provided at opposite lateral sides of a plateau;

FIG. 10 is a schematic illustration explanatory of shadows which are cast in case receded light guide walls are provided at opposite lateral sides of a plateau;

DESCRIPTION OF PREFERRED EMBODIMENTS

Figure 1:
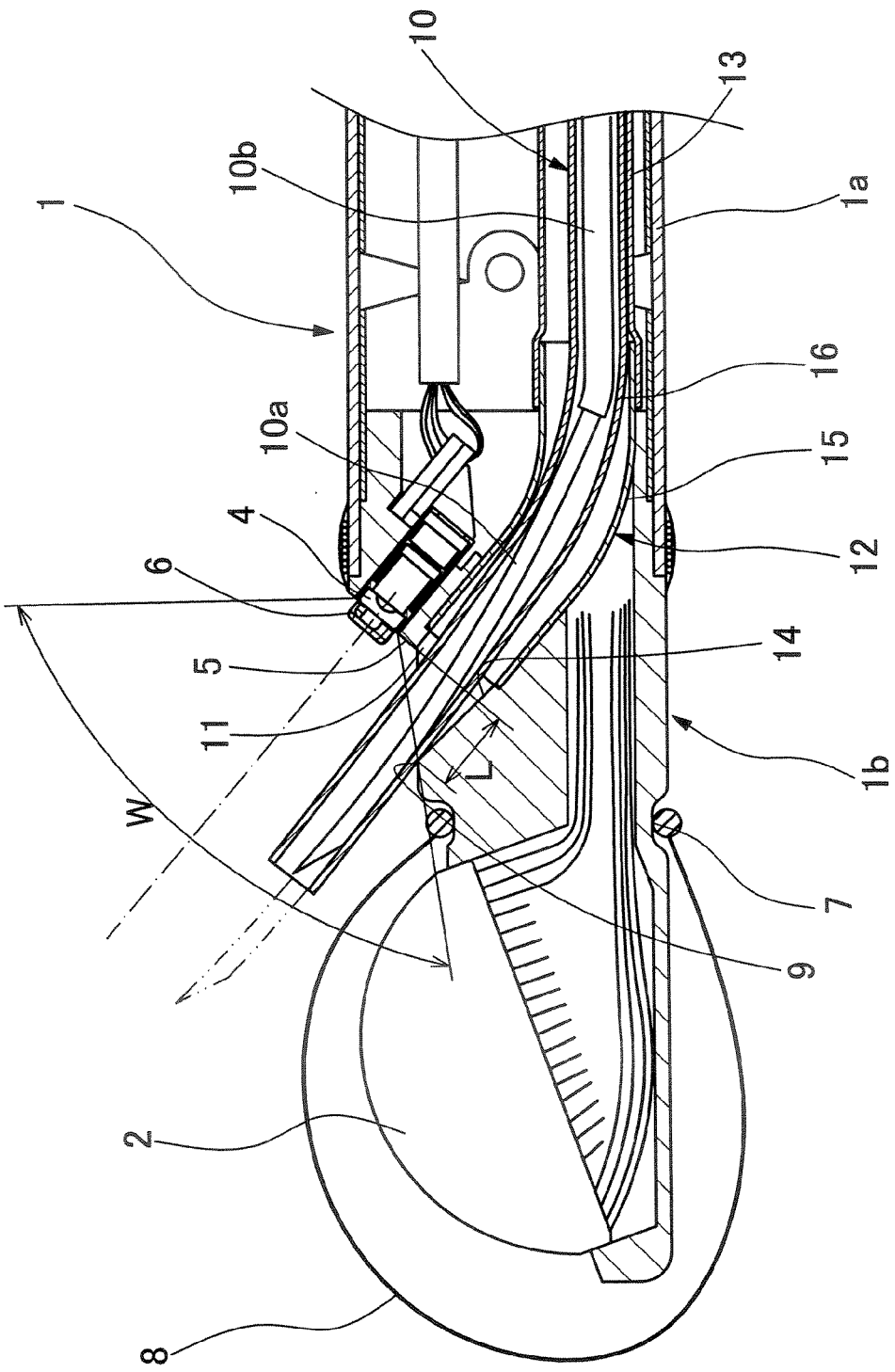
FIG. 1 is a sectional view of a rigid tip end section at the distal end of an insert section of an ultrasound endoscope.
Figure 2:
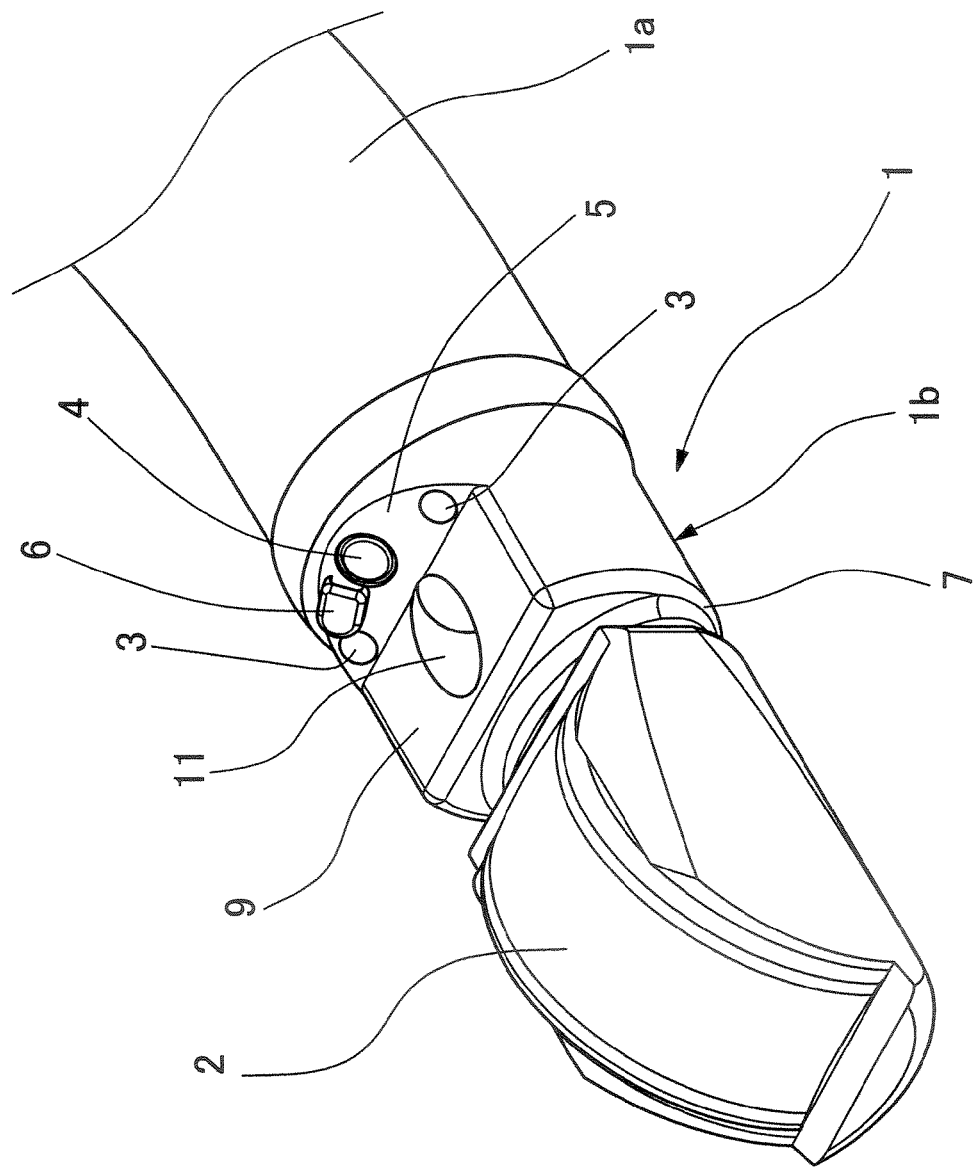
FIG. 2 is a schematic perspective view of the rigid tip end section of the endoscopic insert section.
Figure 3:
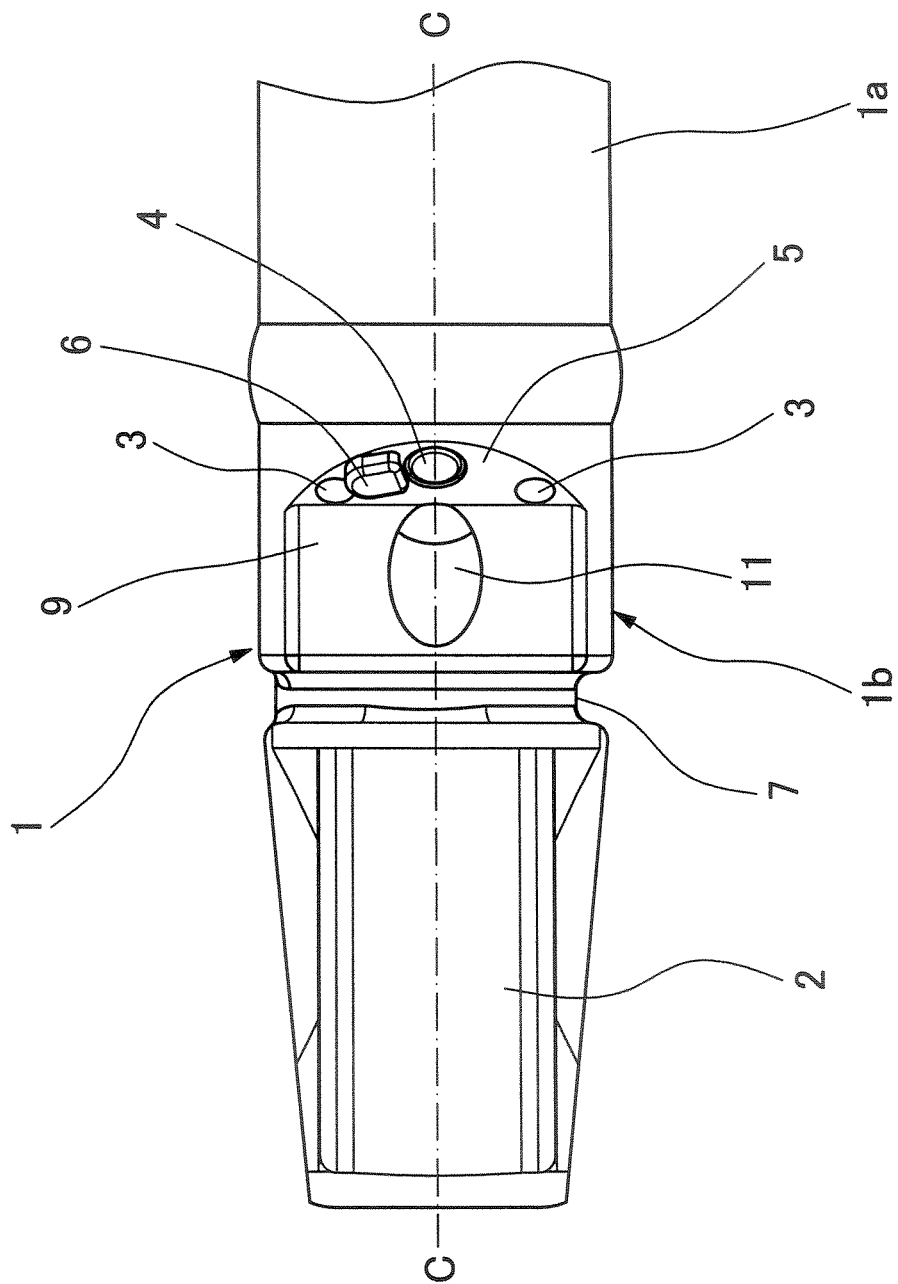
FIG. 3 is a plan view of the rigid tip end section of the endoscopic insert section.
Figure 4:
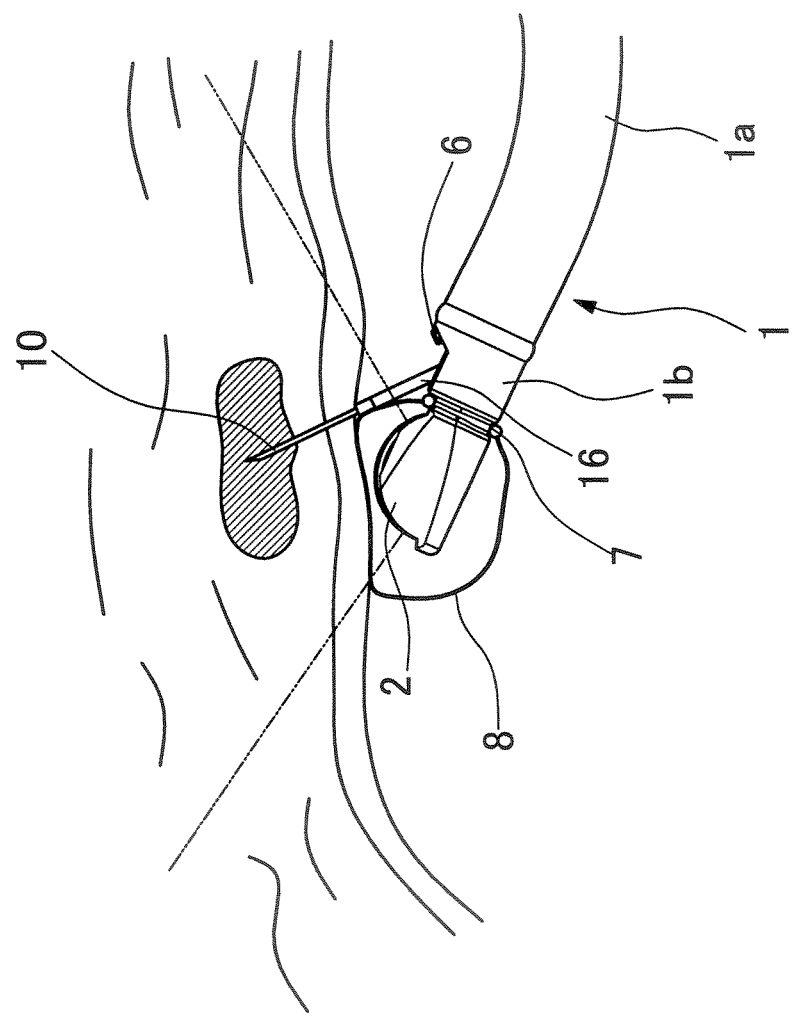
FIG. 4 is a schematic illustration explanatory of an examination by the use of an ultrasound endoscope.

Hereafter, the present invention is described more particularly by way of its preferred embodiments with reference to the accompanying drawings. Referring first to FIGS. 1 to 3, there is shown an ultrasound endoscope according to a first embodiment of the present invention. More specifically, shown in FIG. 1 is a longitudinal sectional view of a rigid tip end section of an endoscopic insert section, and in FIG. 2 a plan view of the same rigid tip end section.

As clear from these figures, an ultrasound examination means and an optical observation means are mounted on a rigid tip end section 1b which connected to the fore end of a bending section 1a of an insert section 1. The ultrasound examination means is constituted by an ultrasound transducer 2 with a large number of ultrasound transducer elements arrayed in the axial direction of the rigid tip end section 1b. The transducer elements of the ultrasound transducer 2 are arranged in an array which is extended axially from a position near a fore distal end of the rigid tip end section 1b toward a proximal end of the same, and in a convexly arcuate shape in the axial direction. These arrayed transducer elements of the ultrasound transducer 2 are driven sequentially at the time of making an ultrasound scan.

On the other hand, the above-mentioned optical observation means is composed of an illumination window or windows 3 and an optical image pickup assembly 4 which are fitted in a inclined casing wall section which is provided in a rear side of the rigid tip end section 1b. That is to say, the inclined casing wall section forms a casing wall section 5 for mounting the optical observation means. The optical image pickup assembly 4 is located approximately centrally of the inclined casing wall section 5, and composed of an objective lens and a solid-state image sensor which is located at the focus of the objective lens. In the particular embodiment shown, a couple of illumination windows 3 are provided on the right and left sides of the optical image assembly 4, each one of the illumination windows 3 being composed of a bundle of fiber optics which feeds light to the illumination window from a light source to which the endoscope is disconnectibly connected, and a diffusion lens which is fitted in a window opening. Further provided on the inclined casing wall section 5 is a wash nozzle 6 for spurting a cleaning fluid toward the optical image pickup.

The rigid tip end section 1b is provided with an annular groove 7 around a casing portion immediately on the proximal side of the ultrasound transducer 2. As shown in FIG. 2, a balloon 8 is anchored in the annular groove 7. The balloon 8 is filled with an ultrasound transmission medium for the purpose of suppressing attenuation of ultrasound signals to a minimum at the time of transmitting ultrasound signals into a patient's body from the ultrasound transducer 2 and also at the time of receiving tomographic echo signals from body tissues.

Also provided on the casing of the rigid tip end section 1b is a plateau 9 which is stretched in the axial direction of the rigid tip end section 1b. More specifically, the plateau 9 is located on the front side of the inclined casing wall section 5 in which the illumination windows 3 and optical image pickup 4 are fitted, and on the rear side of the ultrasound transducer 2, the plateau 9 being provided at a level at least lower than the positions of the illumination windows 3. An instrument outlet opening 11 is opened in the plateau 9 in an obliquely upward direction. A biopsy channel 12 leading to the instrument outlet opening 11 is constituted by an instrument passage tube 13 behind the angle section 1a which is extended substantially parallel with the longitudinal axis of the endoscopic insert section 1. A tunnel-like instrument passage 14 is formed internally of a casing of the rigid tip end section 1b. A fore end portion of a rigid connector pipe of a metal or the like is fitted in the tunnel-like instrument passage 14. In turn, a fore end portion of the instrument passage tube 13 is fitted on a rear end portion of the rigid connector pipe 15. The rigid connector pipe 15 is bent substantially in J-shape to turn the biopsy channel in an obliquely upward direction at the end of the instrument passage tube 13 which is extended in the axial direction of the insert section 1.

Thus, the ultrasound transducer 2, instrument outlet opening 11, and image pickup 4 of the optical observation means are mounted on the rigid tip end section 1b in that order from the fore distal end thereof. As shown in FIG. 3, a tomographic examination area by the ultrasound transducer 2 as well as center of the instrument outlet opening 11 and center of observation by the optical image pickup 4 are located substantially in axially aligned positions on center line C-C. Therefore, a puncture instrument 10 which is led out of the instrument outlet opening 11 of the biopsy channel 12 can be securely captured in the view field of the optical image pickup 4 before intrusion into an intracavitary wall and thereafter in the view field of the ultrasound transducer 2.

By constructing the rigid tip end section 1b as described above, a medical instrument like the puncture instrument 10 can be led out of the instrument outlet opening 11 of the biopsy channel 12 in a stabilized state, aiming at a target point accurately.

As shown in FIG. 1, the puncture instrument 10 inserted in the biopsy channel 12 has a sharp-pointed needle 10a of a metal pipe attached to a fore end of a flexible tube 10b. The puncture instrument 10 is sheathed in a guide tube 16 and retractably projected out of the latter.

When not used, the puncture instrument 10 is placed in the biopsy channel in a standby state with the puncture needle 10a sheathed in the guide tube 10b. In case a disorder is found as a result of an ultrasound scan by the transducer 2, the puncture instrument 10 is driven into the body to sample tissues. As clear from FIG. 1, for sampling body tissues, a fore end portion of the puncture instrument 10 is projected by a predetermined length from the instrument outlet opening 11 with the needle portion 10a in a retracted position, preferably bringing the guide tube 16 into contact with or in close proximity of a target intracavitary wall, and then the puncture instrument 10 is pushed out of the guide tube 16, driving the needle portion 10 into the intracavitary wall.

In this instance, until projected out of the instrument outlet opening 11, the puncture instrument 10 is advanced with its fore end in sliding contact with the inner periphery of the biopsy channel 12, particularly, of the rigid pipe 15 and the terminal passage 14. Since the biopsy channel 12 is inclined relative to the longitudinal axis of the rigid tip end section 1b, it is always the upturned sloped passage portion that the fore end of the puncture instrument 10 is guided by sliding contact. On the rigid tip end section 1b, the plateau 8 is provided contiguously on the front side of the inclined casing wall section 5, and the instrument outlet opening 11 of the biopsy channel 12 is opened in the plateau 8. Therefore, as compared with a case where an instrument outlet opening of a biopsy channel is opened in a downwardly extended portion of a inclined casing wall section, the puncture instrument 10 can be guided over a longer distance increased by a considerable length L as shown in FIG. 1, as it is moved forward under guidance of the sloped portion of the terminal passage 14 starting from the bent portion of the rigid connecting pipe 15. It follows that the puncture instrument 10 can be put in a more stabilized state at the time of aiming same at a target and can be launched with an augmented thrust and with improved controllability at the time of penetration into the body.

The image pickup 4 of the optical observation means has a view angle W as indicated in FIG. 1. Thus, a fore end of the puncture instrument 10 gets into the observation view field of the optical image pickup as soon as it is led out of the instrument outlet opening 11. That is to say, the puncture instrument 10 is captured in the observation view field of the image pickup immediately when it is led out of the instrument outlet opening 11, and, it can be monitored by the ultrasound transducer 2 after penetration into the body and throughout a treatment by the use of the puncture instrument 10. Of course, other medical treating instruments can also be monitored within the observation view field of the image pickup 4, ensuring higher safety as well as higher controllability.

As described above, an inserted medical instrument which has been led out of the instrument outlet opening 11 of the biopsy channel 12 is constantly monitored by the optical image pickup assembly 4 of the endoscope. Since the instrument outlet opening 11 is formed in the plateau 9 which is located at a lower level than the ultrasound transducer 2, a view field of the optical image pickup assembly is partly restricted by a top portion of the ultrasound transducer 2. The plateau 9 is located in a restricted view field area, there is no possibility of the forward view field being further restricted by the instrument outlet opening 11 which is captured in the view field of the optical image pickup assembly 4.

Figure 5:
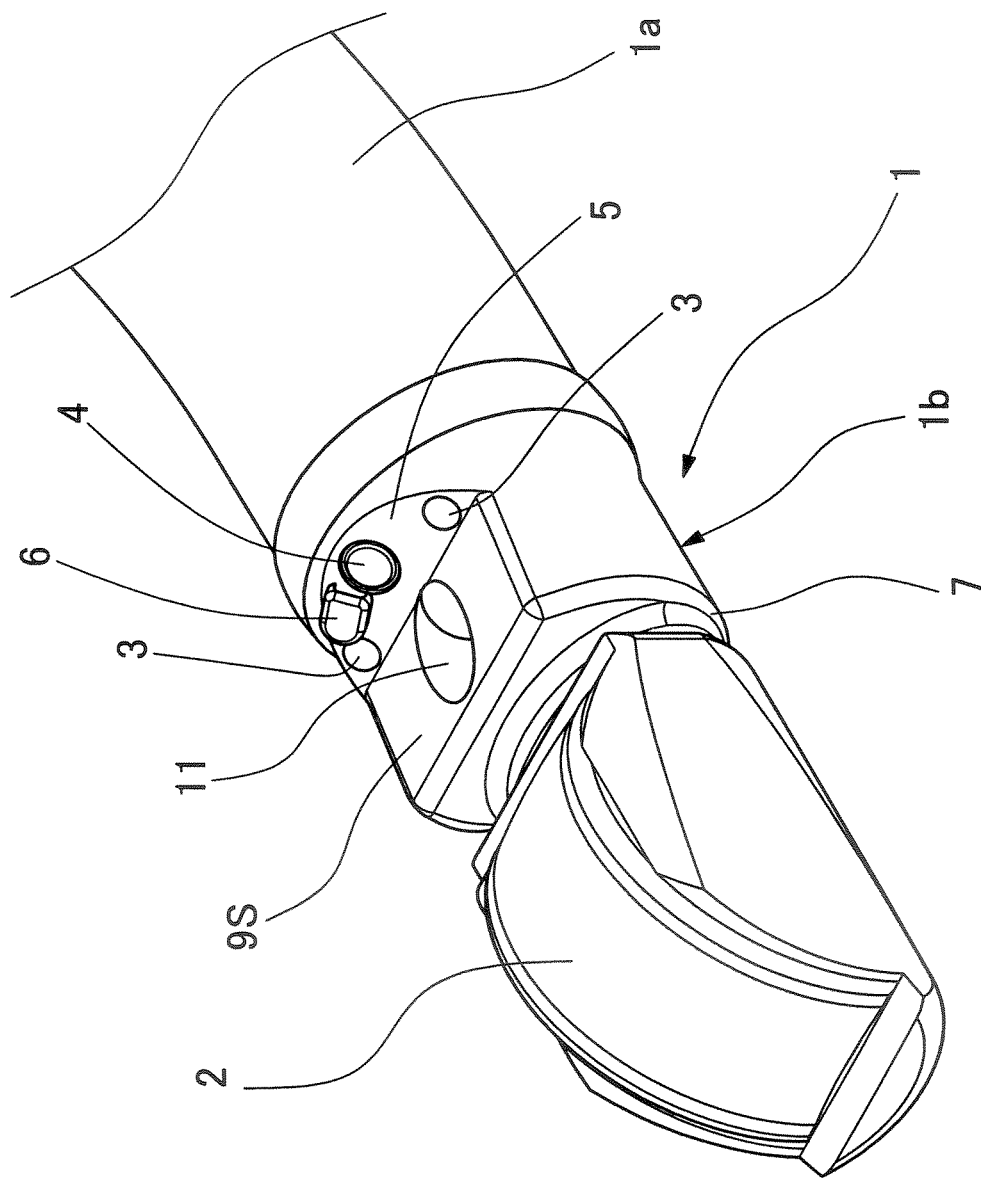
FIG. 5 is a view similar to FIG. 2 but showing a modification of a plateau with a flat top surface.

In this instance, the plateau 8 is formed as a flat surface in the axial direction. The surface of the plateau may be inclined downward toward the inclined casing wall section 5 as in the case of a plateau 9S which is exemplified in FIG. 5.

The inclined casing wall section 5 is shaped arcuately on the upper side when seen from the front side, that is, when seen from side of the distal end of the rigid tip end section 1b, so that the illumination windows 3 on the right and left sides of the optical image pickup assembly 4 are located lower corner portions. Therefore, the two illumination windows 3 are located more closely to the surface of the plateau 9 than the optical image pickup assembly 4, riving rise to a problem as follows.

The optical image pickup assembly 4 has its view filed in an obliquely upward direction, so that illumination light which is projected through the illumination windows 3 should be able to light up intracavitary areas in that direction evenly with the same amount of light. However, in the case of the plateau 9 in the above-described first embodiment, its lateral sides are extended as far as the outer periphery of the rigid tip end section 1b to partly block light from the illumination windows 3, putting lower forward areas in shadow as shown at (a) of FIG. 6. The shadowed areas will be enlarged further especially in a case where the plateau 9 is located closely to the illumination windows 3 to provide an elongated guide passage portion up to the instrument outlet opening 11 to ensure higher stability and controllability in aiming an inserted instrument. As a consequence, as shown at (b) of FIG. 6, hatched areas are put in shadow in the view field VP of the optical image pickup assembly 4. Existence of unilluminated areas or irregularities in illuminating light level, which would result in an unclear image of an intracavitary site under observation, should be suppressed as much as possible.

Figure 7:
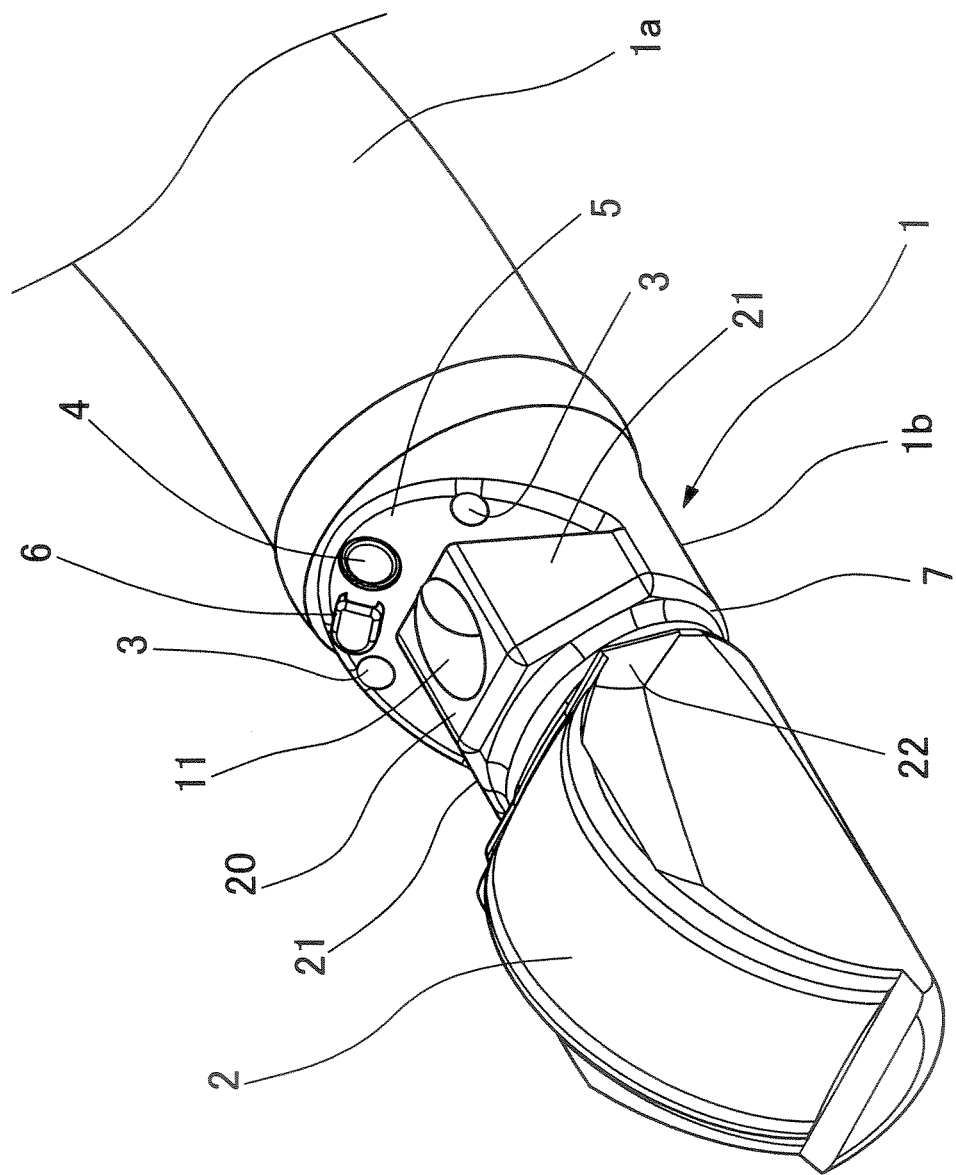
FIG. 7 is a schematic perspective view of a rigid tip end section according to a second embodiment of the present invention.
Figure 8:
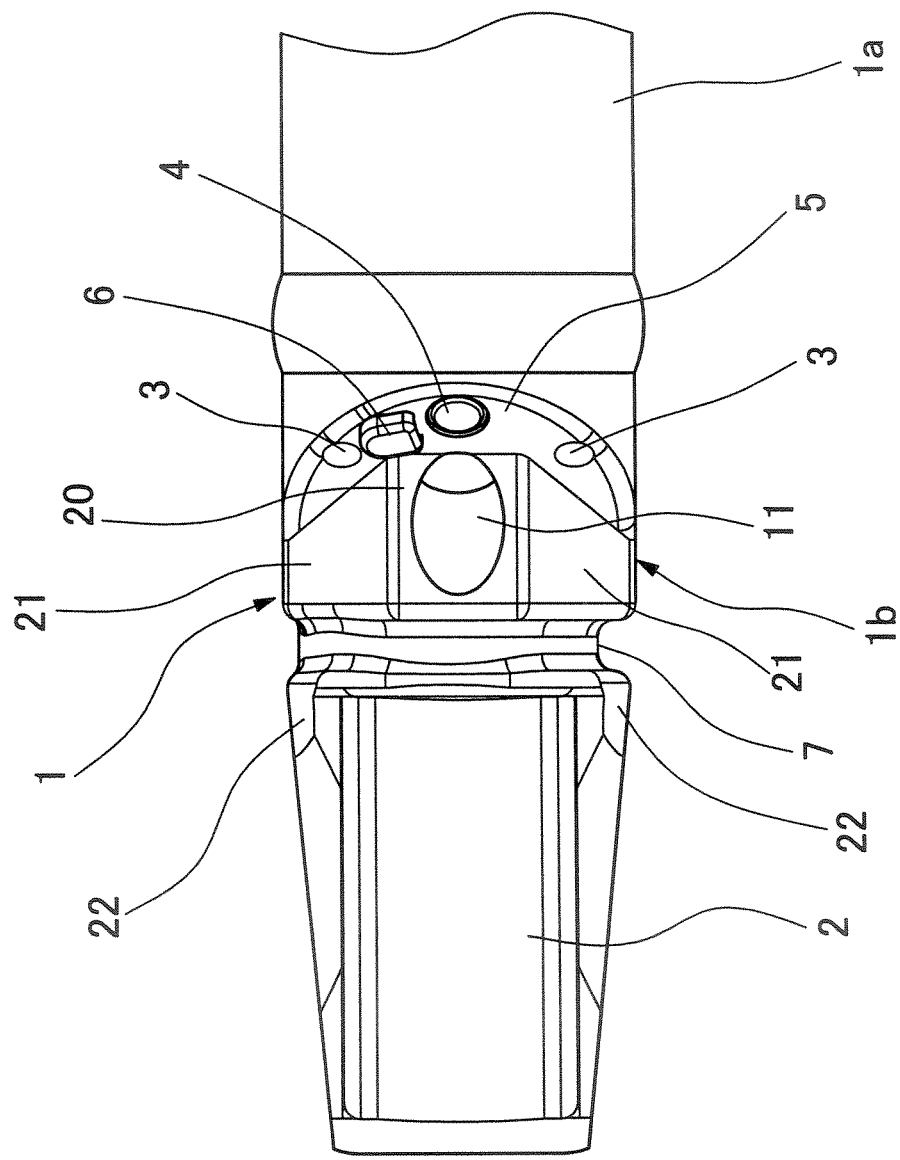
FIG. 8 is a schematic plan view of the rigid tip end section of FIG. 7.
Figure 9:
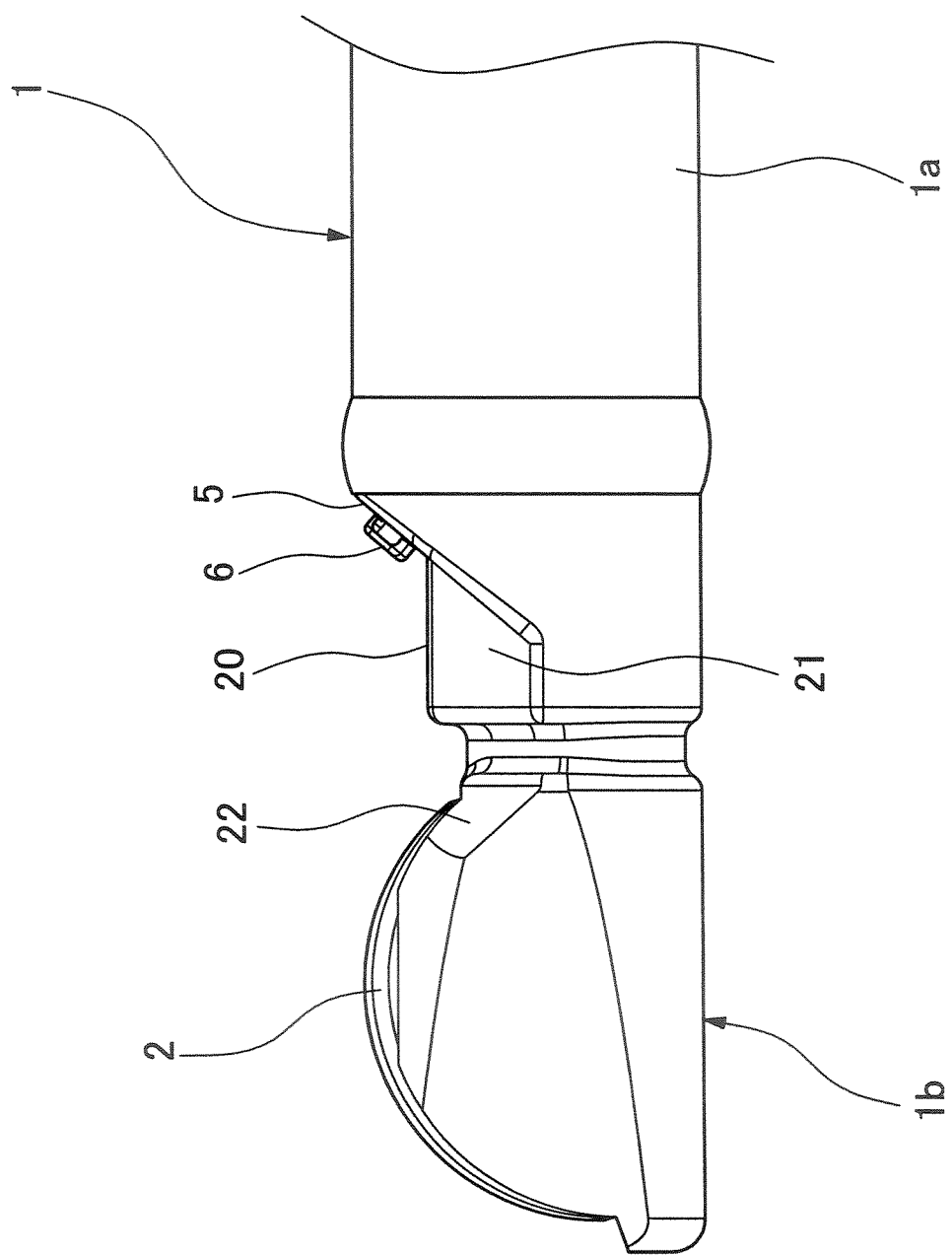
FIG. 9 is a schematic side view of the rigid tip end section of FIG. 7.

In this regard, it suffices for the plateau 9 to have a flat top surface which is wider than the diameter of the instrument outlet opening 11. In other words, the flat top surfaces of the plateau 9 on the opposite sides of the instrument outlet opening 11 are not necessarily required to be extended up to the outer periphery of the rigid tip end section 1b. In a second embodiment shown in FIGS. 7 to 9, opposite sides of a plateau 20 are cut off obliquely to present a trapezoidal shape as a whole. In this case, the flat top surface of the plateau 20 is limited to a minimum area which is necessary for containing the instrument outlet opening 11, and receded light guide walls 21 are provided on the opposite sides of the plateau 20 evade illumination light which is cast from the illumination windows 3. The receded light guide walls 21 at the opposite lateral sides of the plateau 20 are so shaped as to provide a broader unblocked space in front of the illumination windows 3.

As clear from FIG. 1, the rigid pipe 15 is provided on the rigid tip end section 1b as a passage for leading an inserted medical instrument toward the instrument outlet opening 11, but no other components are located on the right and left sides of the rigid pipe 15. Therefore, the provision of the receded light guide walls 21, which are formed by obliquely cutting off the opposite sides of the plateau 20, give rise to no problem in particular. Further, in case lateral sides of a casing portion which accommodates the ultrasound transducer 2 on the rigid tip end section 2b are laterally bulged out on the front side of the illumination windows 3, it is desirable to cut away the laterally bulged portions to provide cutback wall portions 22 on the transducer casing contiguously on the front side of the receded light guide walls 21.

In this manner, by limiting the flat top surface of the plateau 20 to a minimum necessary width for installation of the instrument outlet 11, shadowed areas are minimized as indicated by hatching in FIG. 10(a), to a significant degree as compared with the shadowed areas in the foregoing first embodiment in which the top flat surface of the plateau 9 is extended as far as the outer periphery of the rigid tip end section 1b. As a consequence, illumination light is cast evenly almost on the entire areas in the observation view field of the optical image pickup assembly 4 shown in FIG. 10(b).

Figure 11:
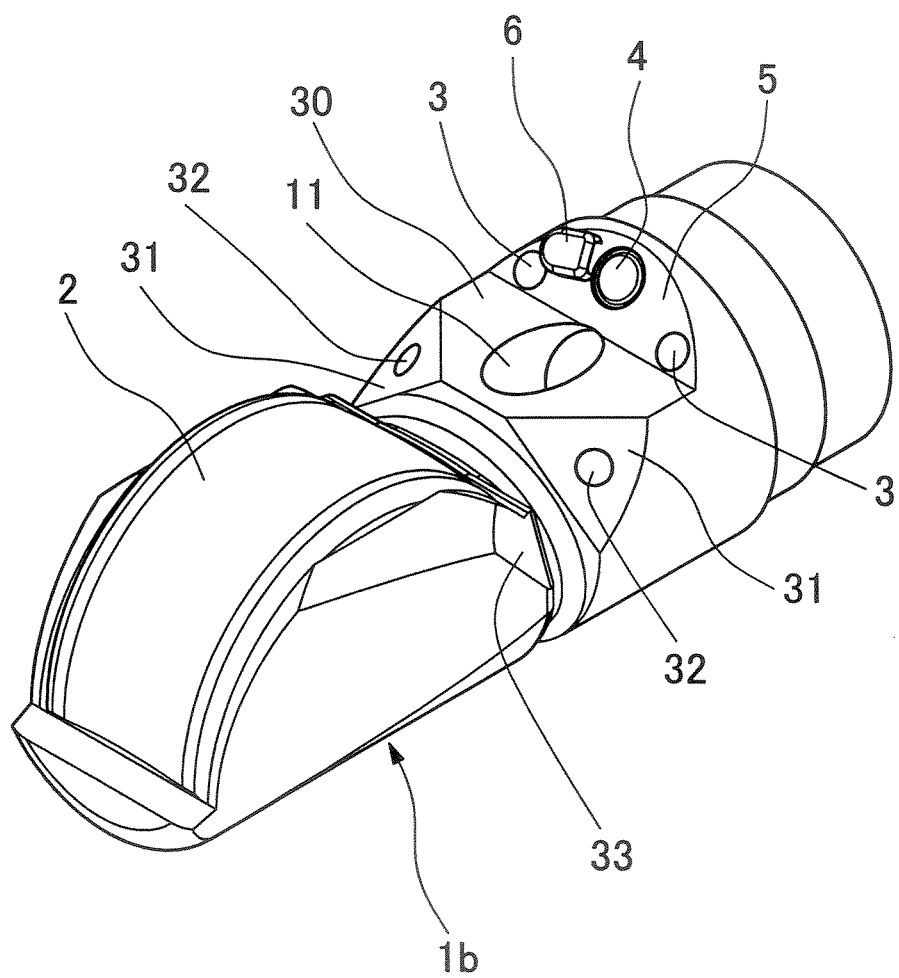
FIG. 11 is a schematic perspective view of a rigid tip end section according to a third embodiment of the present invention.
Figure 12:
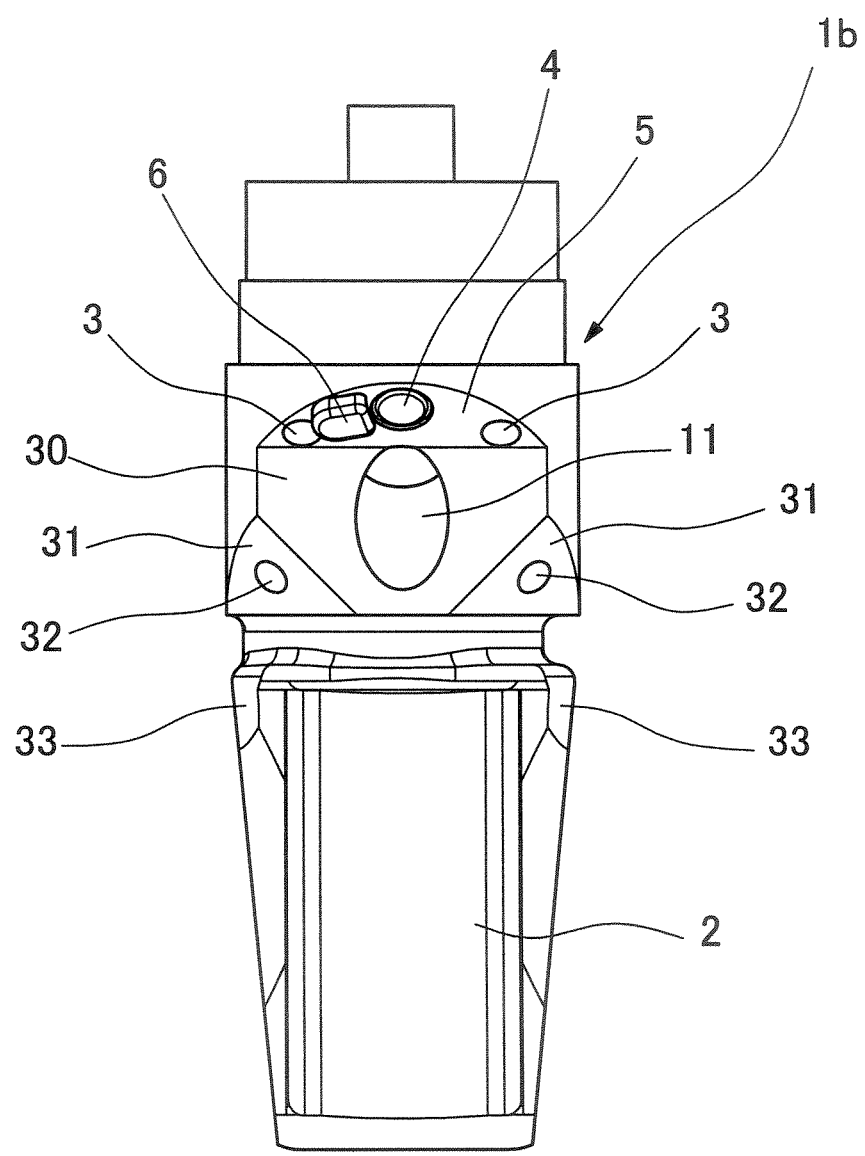
FIG. 12 is a schematic plan view of the rigid tip end section of the third embodiment.
Figure 13:
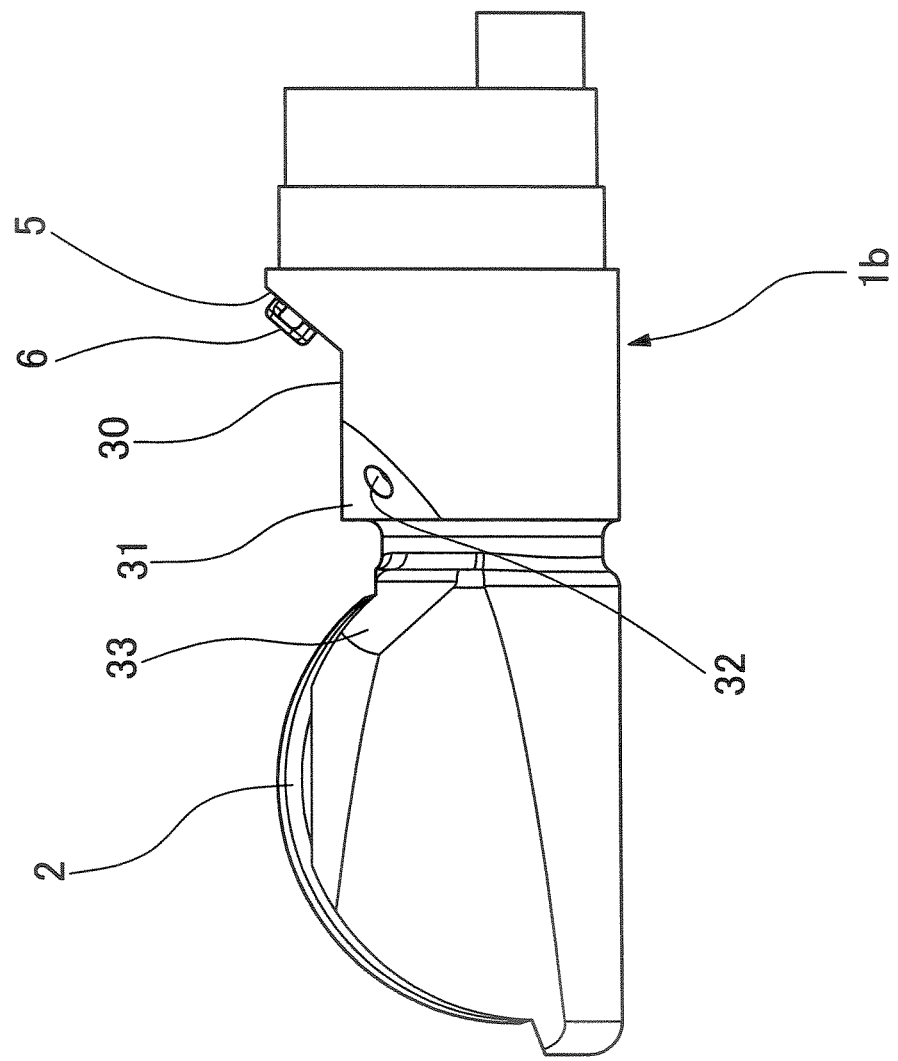
FIG. 13 is a schematic side view of the rigid tip end section of the third embodiment.

Further, shown in FIGS. 11 to 13 is a third embodiment of the present invention. In the third embodiment, for the purpose of suppressing irregularities in illumination light level in the view field of the optical image pickup assembly 4, front corners of a flat top surface of a plateau 30 are obliquely cut away to provide receded light guide wall sections 31, instead of the receded light guide wall sections 21 which are formed by cutting off opposite lateral sides of a plateau 9 in the second embodiment. Of course, in the case of the third embodiment, the fore distal end of the instrument outlet opening 11 is located within the view field of the optical image pickup assembly 4. Further, in the case of the third embodiment, additional illumination windows 32 are provided in the receded light guide wall sections 31.

As described above, the receded light guide walls 31 are provided by obliquely cutting away fore corner portions of the plateau 30 having the instrument outlet opening 11 opened in its flat top surface on the front side of the inclined casing wall section 5 housing the optical image pickup assembly 4, thereby significantly lessening the degree of obstruction or blockage of illumination light. Besides, the illumination windows 32 are provided in the receded light guide walls 31 in addition to the illumination windows 3 which are fitted in the inclined casing wall section 5. Since no blocking wall exists forward of the added illumination windows 32, illumination light can be cast more uniformly to eliminate shadowed areas which are difficult to inspect through the optical image pickup assembly 4. In a case where illumination light is block by a bulged portion at right and left lateral sides of a transducer casing, it is also desirable also in the present embodiment to cut away such laterally bulged portions and to provide cutback wall portions 33 to let the illumination windows 32 cast illumination light over a wider range. In FIGS. 11 to 13 which illustrate the third embodiment of the invention, those component parts which are identical or equivalent with the foregoing second embodiment are designated by the same reference numerals.

What is claimed is:

1. An ultrasound endoscope, comprising:
   an electronic scan type ultrasound transducer having an array of ultrasound elements mounted on a rigid tip end section of an endoscopic insert section in an axial direction thereof;
   an instrument outlet of a biopsy channel opened in a casing of said rigid tip end section in an obliquely upward direction from behind said ultrasound transducer for protruding a medical instrument into a body cavity, and an inclined casing wall section provided further on a rear side of said instrument outlet for fitting optical observation means including two illumination windows and an image pickup assembly provided between said two illumination windows; and
   a plateau provided on said rigid tip end section between said ultrasound transducer and said inclined casing wall section, wherein
   receded light guide walls facing lateral directions are provided on opposite lateral sides of said plateau,
   said receded light guide walls are formed by obliquely cutting opposite lateral sides of said plateau on said rigid tip end section, and
   front corner portions of said plateau are cut off to provide cutback walls each fitted with an additional illumination window.

2. An ultrasound endoscope as defined in claim 1, wherein said ultrasound transducer has a plural number of transducer elements arrayed in a convexly arcuate shape on said rigid tip end section, and said instrument outlet is opened in a flat top surface of said plateau in alignment with a center of a tomographic scan field and a center of an observation view field by said optical image pickup assembly.

3. An ultrasound endoscope as defined in claim 1, wherein said two illumination windows are fitted in said inclined casing wall.

4. An ultrasound endoscope as defined in claim 1, wherein a flat top surface of said plateau is located at a lower level than said illumination windows on said inclined casing wall section, and extended substantially parallel with longitudinal axis of said rigid tip end section.

5. An ultrasound endoscope as defined in claim 1, wherein a flat top surface of said plateau is located at a lower level than said illumination windows on said inclined casing wall section, and raised in forward direction relative to longitudinal axis of said rigid tip end section.

6. An ultrasound endoscope as defined in claim 1, wherein said biopsy channel includes a flexible tube extending in the axial direction of said insert section up to a proximal end portion of said rigid tip end section and having a fore distal end joined with a curved connecting pipe for connection to a terminal passage inclined relative to a longitudinal axis of said rigid tip end section and sloped toward said instrument outlet, and
   a fore end portion of said connecting pipe is placed in said terminal passage of said biopsy channel formed internally of said rigid tip end section, said connecting pipe being bent in a curved shape between a straight rear end portion joined with said flexible tube and a fore end portion providing a sloped guide passage for guiding said inserted medical instrument toward said instrument.

7. An ultrasound endoscope as defined in claim 1, wherein a balloon anchor groove is formed around a proximal end portion of said ultrasound transducer and on a front side of a flat top surface of said plateau.

8. An ultrasound endoscope as defined in claim 1, wherein said receded light guide walls formed by said obliquely cutting said opposite lateral sides of said plateau on said rigid tip end section present a trapezoidal shape as a whole.

9. An ultrasound endoscope as defined in claim 8, wherein said cutback walls are provided at lateral sides of a transducer casing forward of said receded light guide walls.

10. An ultrasound endoscope as defined in claim 8, wherein
said plateau has a flat top surface at a level lower than said ultrasound transducer and said illumination windows of said optical observation means,
said instrument outlet of said biopsy channel is opened in said flat top surface of said plateau,
said flat top surface of said plateau has an area for installation of said instrument outlet of said biopsy channel which is limited to a minimum necessary area for installation of said instrument outlet of said biopsy channel.

\* \* \* \* \*